United States Patent
Landon et al.

(10) Patent No.: US 10,758,360 B2
(45) Date of Patent: Sep. 1, 2020

(54) TIBIAL IMPLANT HAVING AN ANATOMIC STEM

(71) Applicant: Smith & Nephew, Inc., Memphis, TN (US)

(72) Inventors: Ryan L. Landon, Southaven, MS (US); Angela Mines, Mason, TN (US); Ryan Dees, Senatobia, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/400,653

(22) Filed: May 1, 2019

(65) Prior Publication Data

US 2019/0254830 A1 Aug. 22, 2019

Related U.S. Application Data

(62) Division of application No. 14/386,152, filed as application No. PCT/US2013/032115 on Mar. 15, 2013, now Pat. No. 10,335,284.
(Continued)

(51) Int. Cl.
*A61F 2/38* (2006.01)
*A61F 2/30* (2006.01)

(52) U.S. Cl.
CPC ............ *A61F 2/389* (2013.01); *A61F 2/3886* (2013.01); *A61F 2002/30878* (2013.01); *A61F 2002/30884* (2013.01)

(58) Field of Classification Search
CPC .. A61F 2002/30884; A61F 2002/30879; A61F 2/389
See application file for complete search history.

(56) References Cited

U.S. PATENT DOCUMENTS

| 4,895,571 A | 1/1990 | Grundei |
| 5,137,536 A | 8/1992 | Koshino |

(Continued)

FOREIGN PATENT DOCUMENTS

| CA | 2490963 C | 6/2005 |
| EP | 1413624 A1 | 4/2004 |

(Continued)

OTHER PUBLICATIONS

Canadian Office Action; Canadian Intellectual Property Office; Canadian Patent Application No. 2,868,087; dated Dec. 3, 2018, 4 pages.
Australian Examination Report; Australian Intellectual Property Office; Australian Patent Application No. 2017245436; dated Oct. 23, 2018; 4 pages.
(Continued)

*Primary Examiner* — Bruce E Snow

(57) ABSTRACT

Disclosed herein are systems, methods, and devices for providing a tibial implant including an anatomic stem that provides a close interface between the implant and surrounding bone. The stem varies in size, cross-sectional shape, or orientation from a proximal portion of the stem to the tip of the stem. The variation of the stem accommodates the variation of tibial anatomy into which the implant component is implanted. The stem provides resistance against rotation of the implant and reduces stress shielding effects by transmitting forces into surrounding bone. In certain implementations, the interface between the stem and bone is supplemented by fin extensions that extend outward from the stem and increase the contact between the implant and the surrounding bone structure.

19 Claims, 7 Drawing Sheets

Related U.S. Application Data

(60) Provisional application No. 61/613,733, filed on Mar. 21, 2012.

(56) References Cited

U.S. PATENT DOCUMENTS

| | | | |
|---|---|---|---|
| 5,271,737 | A | 12/1993 | Baldwin et al. |
| 5,782,920 | A | 7/1998 | Colleran |
| 6,102,955 | A | 8/2000 | Mendes et al. |
| 6,149,687 | A | 11/2000 | Gray |
| 6,923,832 | B1 | 8/2005 | Sharkey et al. |
| 7,998,217 | B1 | 8/2011 | Brown |
| 8,016,891 | B2 | 9/2011 | Ensign |
| 2004/0034432 | A1 | 2/2004 | Hughes et al. |
| 2007/0010890 | A1* | 1/2007 | Collazo ............ A61F 2/389 623/20.15 |
| 2007/0179628 | A1 | 8/2007 | Rochetin |
| 2008/0183177 | A1 | 7/2008 | Fox et al. |
| 2009/0204222 | A1 | 8/2009 | Burstein et al. |
| 2010/0023015 | A1 | 1/2010 | Park |

FOREIGN PATENT DOCUMENTS

| | | | |
|---|---|---|---|
| GB | 2423025 | A | 8/2006 |
| JP | H11-47174 | A | 2/1999 |
| JP | 2009515610 | A | 4/2009 |
| WO | 2005034818 | A1 | 4/2005 |
| WO | 2007053905 | A1 | 5/2007 |

OTHER PUBLICATIONS

Japanese Office Action; Japanese Patent Office; Japanese Patent Application No. 2015-501807; dated Oct. 1, 2018; 7 pages.
State Intellectual Property Office, Fourth Office Action, dated Oct. 20, 2017, 10 pages including English Translation.
Japanese Patent Office, Second Office Action, dated Oct. 16, 2017, 7 pages including English Translation.
China Patent Office, Third Office Action, dated Mar. 2, 2017, 20 pages including English Translation.
Japanese Patent Office, First Office Action, dated Jan. 23, 2017, 6 pages including English Translation.
Australian Patent Office, Patent Examination Report No. 1, dated Oct. 20, 2016, 4 pages.
European Patent Office, First Office Action, dated Sep. 13, 2016, 6 pages.
China Patent Office, Second Office Action, dated Jul. 4, 2016, 16 pages including English translation.
China Patent Office, First Office Action, dated Sep. 6, 2015, 21 pages including English translation.
European Search Report, dated Sep. 14, 2015, 6 pages.
International Search Report and Written Opinion, PCT Application No. PCT/US2013/32115, dated Jun. 26, 2013.
Examination Report for Indian Patent Application No. 7700/DELNP/2014, dated Dec. 30, 2019.
Canadian Office Action; Canadian Intellectual Property Office; Canadian Patent Application No. 2,868,087; dated Sep. 17, 2019, 4 pages.

\* cited by examiner

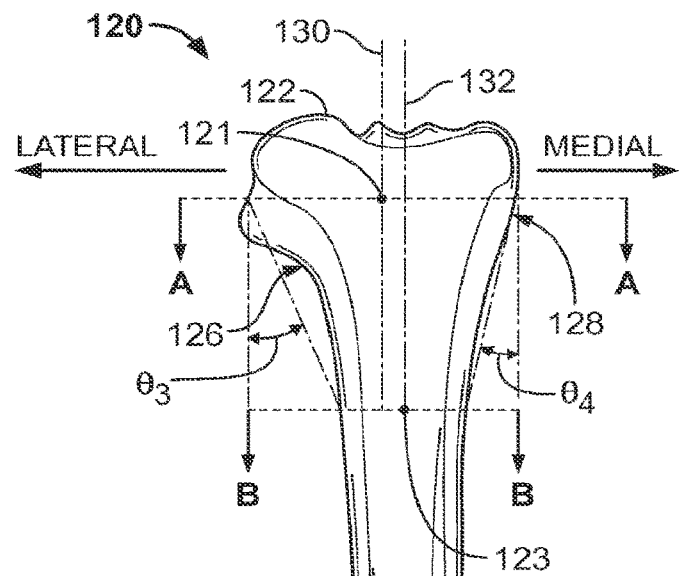
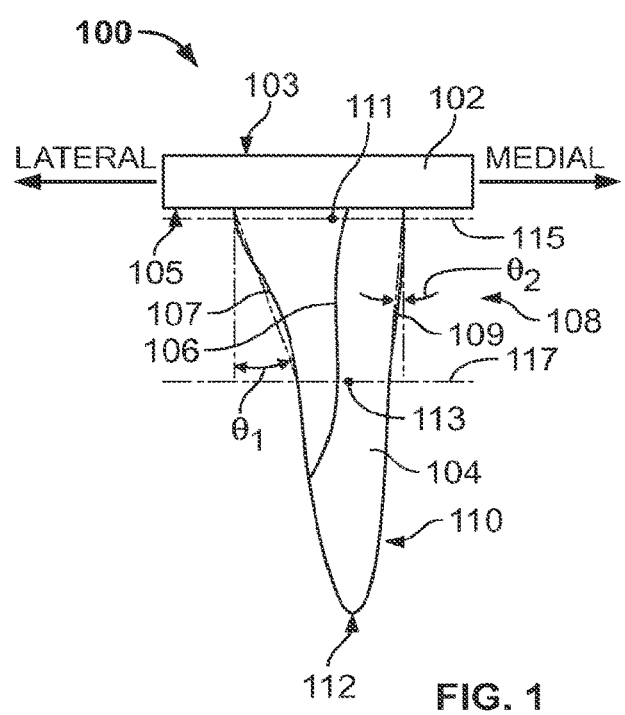
FIG. 1
FIG. 2

TIBIAL IMPLANT HAVING AN ANATOMIC STEM

CROSS-REFERENCE TO RELATED APPLICATION

This application is a divisional of pending U.S. patent application Ser. No. 14/386,152, filed Sep. 18, 2014, entitled "Tibial Implant Having an Anatomic Stem", which is a United States National Stage filing under 35 U.S.C. § 371 of International Application No. PCT/US2013/032115, filed on Mar. 15, 2013, which claims the benefit of U.S. Provisional Patent Application No. 61/613,733, filed Mar. 21, 2012, each of which is hereby incorporated by reference herein in its entirety. International Application No. PCT/US2013/032115 was published under PCT Article 21(2) in English.

BACKGROUND

Knee implants are often used to replace knees that become disabled or cause a patient pain due to normal wear of the bone or due to degenerative disease. A total knee replacement involves replacement of the native bone with at least two components: a femoral component to replace the distal end of the femur, and a tibial component to replace the proximal end of the tibia. The femoral and tibial components are positioned and designed to mimic the native bone and provide an articulation interface that allows normal anatomic movement of the knee joint following implantation surgery.

A standard tibial implant includes two main portions—a tray and a stem. The proximal portion of the tibial implant is a tray that forms the articulation interface with a femoral component. Often, the tray holds a liner made of a compliant material, such as polyethylene, that provides a smooth surface for articulation with the femoral component. The distal portion of the tibial implant forms a stem that is designed to extend down into a tibia into which the component is implanted. In order to provide normal anatomic movement of the knee implant, the tibial implant must be held firmly in place to prevent the implant from moving down further into the bone and also from rotating in place within the bone.

In order to resist movement of the tibial implant relative to the bone, the implant must form a strong interface with the bone into which it is being implanted. During implantation, the interface between the implant and the bone is first formed by an initial fixation, for example with bone screws or cement, when the tibial component is first placed into the bone. The initial fixation is sometimes supplemented by later ingrowth of the surrounding bone into the surfaces of the implant if the implant includes textured ingrowth surfaces. This ingrowth can provide some resistance to rotation and subsidence of the tibial component down into the bone. However, the cancellous bone that grows into the implant surface is soft, spongy bone that is able to resist only small forces. A substantial force applied to the implant can break the interface of the bone and the ingrowth surface, leading to subsidence and rotation of the tibial tray.

In some current approaches, the stem of a tibial implant is placed into the cancellous bone of a patient's tibia, and the areas between the implanted component and the hard cortical bone are filled with cement. While this cement provides a connection between the implant and the stronger cortical bone, the cement is often not strong enough to provide the initial and long term fixation and resistance against subsidence and rotation that is needed to resist high forces that can occur during normal use of a total knee arthroplasty. As with cancellous bone ingrowth, the cement interface can be broken by these forces, and the implant function can be compromised by the effects of stress shielding and subsidence.

SUMMARY

Disclosed herein are systems, devices and methods for providing a tibial implant that includes an anatomic stem that forms a geometrically defined interface between the implant and the cortical bone of a patient's tibia. The systems, devices and methods also provide tibial implants that contact and transmit forces incident on the implant to surrounding bone. The interface provides physical presence in areas and regions of the tibia bone that support improved fixation on the implant while still transferring adequate stress to both the cancellous and cortical bone to ensure that the bone remains strong. Thus, the interface between the implant and the cortical bone can help reduce the occurrence of stress shielding and subsidence into the tibial bone while also resisting rotation of the tibial implant in the bone.

According to some embodiments, a tibial implant includes a tray configured to abut a patient's bone and a stem extending from a surface of the tray. The stem has a proximal portion at which a first cross-section of the stem has a first shape and a first center positioned at a first location relative to the tray, and a distal portion at which a second cross-section of the stem has a second shape and a second center positioned at a second location relative to the tray.

In certain implementations, at least one of the first and second cross-sections includes a corner configured to engage the patient's bone, for example an interior surface of the patient's cortical bone. In certain implementations, the first cross-section includes a first corner that extends at a first angle relative to the longitudinal axis of the stem, and the second cross-section includes a second corner that extends at a second angle relative to the longitudinal axis of the stem. The first and second angles correspond to an anatomic landmark at each of the first and second cross-sections.

In certain implementations, the center of the second cross-section is located anterior relative to the center of the first cross-section. In certain implementations, the center of the second cross-section is located medial relative to the center of the first cross-section. In certain implementations, the center of the second cross-section is located posterior relative to the center of the first cross-section. In certain implementations, the second cross-section has a smaller area than the first cross-section.

In certain implementations, the implant includes a fin extending outward from the stem. The fin extends from an inferior surface of the tray, and an inferior perimeter of the fin includes a tapping mechanism configured to cut into the patient's bone. The implant also includes a plurality of engagement portions extending from the fin. The fin extends from the stem at a first angle relative to a longitudinal axis of the stem, and each of the plurality of engagement portions extends from the fin at a second angle perpendicular to the first angle. The engagement portions include at least one of circular projections, triangular projections, square projections, and sawtooth projections. An outer portion is shaped to engage the patient's bone, and the outer portion of the fin may include a cloverleaf shape or a hook shape.

In certain implementations, the implant includes first and second cross-sections that include corners that are offset relative each other based on second cross-sections of a cortical bone. A bounding box may be defined by four line segments along the peripheries of the first and second cross-sections, and the line segments may be connected by four or more radial segments. The first and second cross-sections may have an aspect ratio between approximately 1.0 and approximately 2.0. The long axis of the second cross-section may be rotated relative to a long axis of the first cross section. The second cross section may be rotated less than 70.degree. relative to the first cross section. In certain implementations, the first and second cross-sections of the implant are optimized to target both maximum and minimum bone sizes while maintaining a defined offset to cortical bone.

BRIEF DESCRIPTION OF THE DRAWINGS

The foregoing and other objects and advantages will be appreciated more fully from the following further description thereof. With reference to the accompanying drawings, these depicted embodiments are to be understood as illustrative and not as limiting in any way.

FIG. 1 shows a front view of an illustrative tibial implant having an anatomic stem;

FIG. 2 shows an anterior view of an illustrative tibia bone;

DETAILED DESCRIPTION

Figure 3:
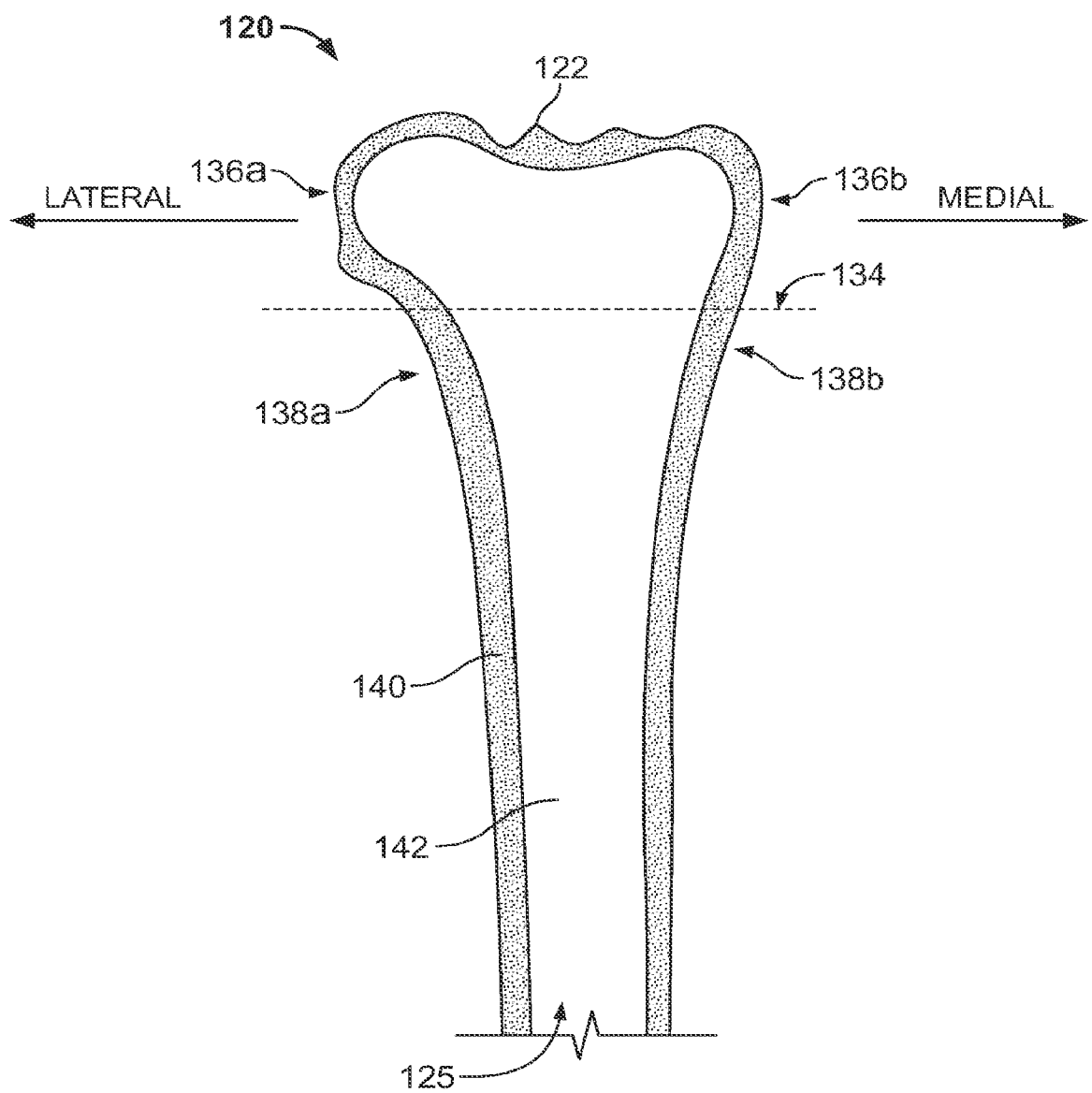
FIG. 3 shows an illustrative longitudinal cross-section of a proximal portion of the tibia bone shown in FIG. 2.

To provide an overall understanding of the systems, devices and methods described herein, certain illustrative embodiments will now be described. For the purpose of clarity and illustration these systems and methods will be described with respect to orthopedic tibial implants. It will be understood by one of ordinary skill in the art that the systems, devices and methods described herein may be adapted and modified as is appropriate, and that these systems, devices and methods may be employed in other suitable applications, such as for other types of joints and orthopedic implants, and that other such additions and modifications will not depart from the scope hereof.

FIG. 1 shows a front view of a tibial implant 100 having a base plate 102 and an anatomic stem 104. In the depicted embodiment, the tibial implant 100 having the base plate 102 and the anatomic stem 104 is monolithic. The implant 100 is configured to be implanted into a patient's tibia with the base plate 102 disposed at the proximal end of the tibia. In this position, the top surface 103 of the base plate 102 forms an articulation interface with a patient's femoral bone or an implant placed into the native femoral bone. A liner made of a compliant material, such as polyethylene, is coupled with the top surface 103 to provide a smooth articulation surface. The bottom surface 105 of the base plate 102 forms an interface with the tibial bone into which the implant 100 is implanted. The bottom surface 105 contacts a proximal surface of the tibial bone and is affixed to the bone by cement, bone screws, growth of the tibial bone into a textured surface, or a combination thereof.

The anatomic stem 104 of the implant 100 extends from the bottom surface 105 and is designed to form a geometrically defined interface with the tibial bone into which it is implanted. In particular, the stem is designed to substantially extend longitudinally through the center of the tibial intramedullary cavity, transmit longitudinal and radial forces into surrounding bone, preferably in a way that disperses the forces equally, and maintain a close interface with the cortical bone. The combination of these features helps strengthen the bone to reduce stress shielding effects and subsidence of the base plate 102 further down into the tibia, and helps resist rotation of the implant 100 when torsional forces are applied to the implant 100.

A standard tibia bone exhibits a changing anatomy as it extends distally from the proximal end of the bone. In particular, the size, center, and shape of the inner intramedullary cavity, formed of spongy cancellous bone, vary throughout the tibia. In order to maintain a close contact with the bone, the anatomic stem 104 is varied from the bottom surface 105 of the base plate to the tip 112 of the stem to accommodate the changing anatomy. For example, an upper portion 108 of the stem 104 is tapered from proximal level 115 to distal level 117, and a lateral side 107 of the upper portion tapers at an angle $\theta_1$ that is greater than the angle $\theta_2$ at which a medial side 109 of the upper portion tapers. This taper shifts the center of the stem 104 longitudinally along the stem to maintain the alignment of the stem 104 with the changing position of the center of the intramedullary cavity. In particular, at the proximal level 115, the center is center point 111, and at the distal level 117, the center is at center point 113, which is shifted medially from center point 111. The stem 104 also has a rounded corner 106 that shifts laterally relative to the longitudinal axis of the stem from the upper portion 108 to the lower portion 110 of the stem 104 in order to accommodate the anatomy of the anterior portion of the tibia to maintain a close contact with the hard outer cortical bone of the tibia. While the stem 104 in FIG. 1 shows a lateral side having a sharper taper angle $\theta_1$ than the angle $\theta_2$ on the medial side, the taper angles of the stem may vary to accommodate varying patient tibial anatomies. In other implementations, the stem 104 may taper at approximately the same angle on both medial and lateral sides. As a result, the center points 111 and 113 may be co-located and not shifted relative to each other, or may shift only in an anterior or a posterior direction. Alternatively, the stem 104 may taper on the medial side at an angle $\theta_2$ that is sharper than angle $\theta_1$ on the lateral side. As a result, the center of the stem will shift in a lateral direction moving distally down the stem.

FIG. 2 shows a front view of a tibial bone 120 and its anatomical variations that the stem 104 is designed to accommodate. The bone 120 has a proximal end 122 and a distal end 124. The anatomy of the bone 120 and, in particular, the shape and location of the center of the intramedullary cavity of the bone 120 may vary from the proximal end 122 to the distal end 124. The bone 120 narrows from the proximal end 122 as the lateral side 126 and medial side 128 of the bone taper toward the center of the bone 120. As can be seen in FIG. 2, the lateral side of the bone 126 tapers at an angle $\theta_3$ toward the center of the bone 120, which is sharper than the angle $\theta_4$ at which the medial side 128 tapers. As a result, the center of the bone and the intramedullary cavity inside the bone shift in a medial direction. The movement of the intramedullary cavity is shown by the center axes 130 and 132, taken at different levels of the bone 120 shown by lines AA and BB. The center axis 130 passes through proximal center point 121 at proximal line AA, while the axis 132 passes through the distal center point 123 of the bone 120 at distal line BB. As shown in FIG. 2, the center axis moves slightly towards the medial side of the bone as a result of the sharper tapering angle of the lateral side of the bone 120. While the center of the cavity shifts medially in bone 120, patient tibial anatomies may vary naturally or due to certain medical conditions and thus the shift of the cavity may vary across a population. In other bones, the tibia may taper at approximately the same angle on medial and lateral sides, or the medial side may taper at a sharper angle than the lateral side. Additionally, the intramedullary cavity may exhibit a different change than the outer cortical bone. Regardless of the tapering of the medial and lateral sides of the tibial cortical bone, the center of the intramedullary cavity may shift either medially or laterally, and either posteriorly or anteriorly, moving distally down the bone.

The changes in the external anatomy of the tibia shown in FIG. 2 cause corresponding changes in the size, location, and shape of the inner cancellous bone of the tibia. FIG. 3 shows a front view of a longitudinal cross-section taken of the bone shown in FIG. 2, exposing the interior cancellous bone 142. The outer shell of cortical bone 140 surrounds the spongy cancellous bone 142. The changes in the intramedullary cavity caused by the changes in anatomy moving away from the proximal end 122 of the bone 120 are highlighted by the nonsymmetrical shape of the cancellous bone 142. The tapering of the lateral and medial sides of the cortical bone 140 causes the cancellous bone 142 to become narrower in the distal tibia. The uneven tapering of the lateral and medial sides also shifts the center of the cancellous bone 142 medially in the distal tibia. In other bones, the tapering of medial and lateral sides of the cortical bone may be about equal, and the center of the cancellous bone 142 may shift either medially or laterally, or may not shift in a medial or lateral direction.

An anatomical stem designed to contour to the inner shapes of the bone 120 can be designed by creating two main portions—one portion corresponding to a wider proximal region of the bone and one portion corresponding to a narrower distal portion of the bone. A critical point on the tibial anatomy, such as a point corresponding to a shape change or other physical transition, can be identified and used to determine the size and design of the two portions of the stem. In some implementations, one portion is designed to accommodate the proximal anatomy above the critical point and one portion designed to accommodate the distal anatomy below the critical point. An example of such a critical point is shown in FIG. 3 by the transverse line 134. The transverse line 134 separates a top portion and a bottom portion of the bone 120 at an inflection point on the medial and lateral sides of the bone 120. In the region of the bone 120 above the line 134, the medial and lateral sides of the bone 120 exhibit a concave shape as shown on the lateral side by the bone portion 136a and medial side by bone portion 136b. Below the line 134, the medial and lateral sides of the bone exhibit a concave shape, as shown by lateral bone portion 138a and medial bone portion 138b. In certain implementations, an anatomic stem is designed using the inflection point indicated by line 134 as a critical point and structuring the stem to have an upper portion such as the upper portion 108 of implant 100, which is designed to accommodate the shape and size of the intramedullary cavity above the inflection point and a second portion of the stem, such as the lower portion 110 of the implant 100 designed to accommodate the shape and size of the intramedullary cavity below the inflection point. The line 134 corresponds to the shape or other physical transition that in turn corresponds to the change or transition in the bone's structure. Though the exact location of the inflection point and the line 134 varies from bone to bone and patient to patient, the shape of a tibial bone does not vary significantly and thus the line 134 does not vary significantly from patient to patient. Thus, structuring a stem based on such a point can provide a better fit for a larger number of patients.

In addition to the size and the changing center of the intramedullary cavity, the cross-sectional shape of the bone 120 changes along its structure from the proximal end 122 to the distal portion 125. This change in shape can be shown by viewing transverse cross-sections at different levels of the bone 120. For example, one cross-section can be viewed above a critical point of a tibia, and a second cross-section can be viewed below the critical point. By using one cross-section above the line 134 and cross-section below the line 134, for example cross-sections taken at lines AA and BB in FIG. 2, one can highlight the differing shapes of the bones for which the different portions of an anatomic stem is designed. Although the size, shape, and center of the intramedullary cavity may change, other characteristics such as the aspect ratio of the cavity, and of an anatomic implant designed to accommodate the cavity geometry, may remain generally constant at various levels of the cavity. For example, the aspect ratio of intramedullary cavities across a population of bone geometries may fall within the range of about 1.0 to about 2.0 even as shape and size of the intramedullary cavity varies at different levels of the bones. The aspect ratio of the cavity and anatomic implants is discussed below with respect to FIG. 9.

Figure 4A:
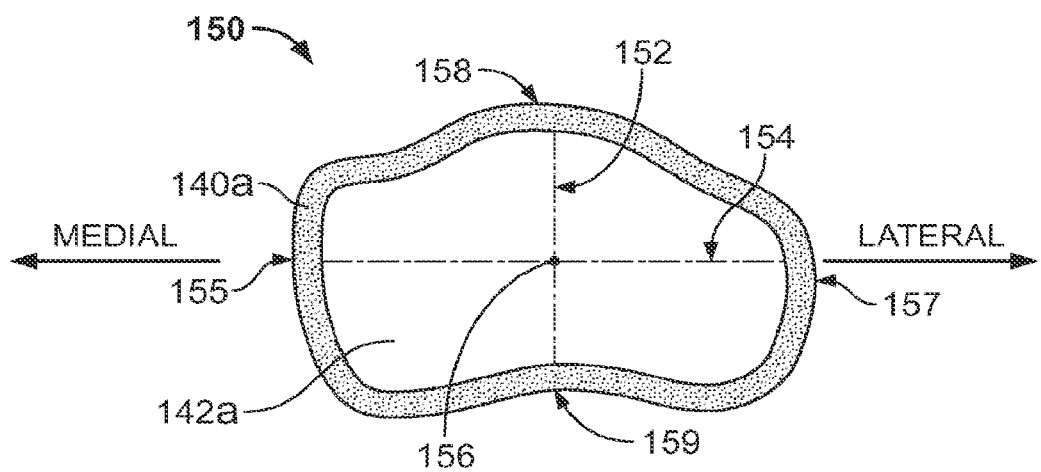
FIGS. 4A and 4B show illustrative transverse cross-sections of the tibia bone shown in FIG. 2.

FIG. 4A shows a cross-section 150 of the bone 120 taken at the level AA indicated in FIG. 2, which is above the inflection point discussed above with respect to FIG. 3. The cross-section 150 shows the outer cortical bone 140a surrounding the intramedullary cavity formed by the cancellous bone 142a along with a major axis 154 and minor axis 152 that cross at the center point 156 of the intramedullary cavity. Due to the shape of the cortical bone 140a, the center point 156 is not equidistant from the anterior and posterior sides of the bone, nor is the center point 156 equidistant from the medial and lateral sides of the bone. Thus, a stem which is merely symmetrical and designed to hit the center point 156 of the inner cavity is not able to form a close interface in all directions with the cortical bone 140a.

The center point 156 is not equidistant from the sides of the cortical bone 140a because of the nonsymmetrical shape of the bone at cross-section 150. In the anterior-posterior direction, the cortical bone 140a extends in the anterior direction on the anterior side of the bone to form a tibial tuberosity 158 that is standard for the tibial anatomy, and there is an indent formed on the posterior side 159 side of the bone. The positioning of the notch and the tuberosity cause the center point 156 of the two axes to be closer to the posterior side of the bone than the anterior side. In addition, the nonsymmetrical shape of the cortical bone 140a creates a wider area of cancellous bone between the center point 156 and both the lateral side 157 of the bone and medial side 155 of the bone than between either of the center point 156 and the anterior or posterior sides 158 and 159. A stem designed to form a close contact with the cortical bone 140a and occupy a significant portion of the cavity within the cortical bone 140a preferable accommodates these nuances of the anatomy.

Figure 4B:
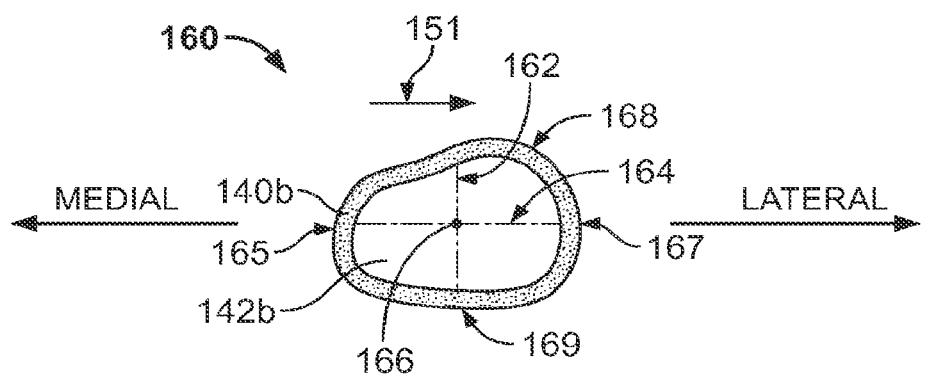

Viewing transverse cross-sections at various levels along the longitudinal axis of the bone 120 highlights the change in the size and shape of the inner cavity of the bone as well as the different positions of the center point of the bone. FIG. 4B shows a cross-section 160 taken at the level indicated by line BB in FIG. 2, which is below the inflection point depicted in FIG. 3. The cross-section 160 shows the cortical bone 140b and cancellous bone 142b of the tibial bone 120, and the shape of cross-section 160 is different than the cross-section 150. A major axis 164 and a minor axis 162 are shown in the cross-section 160, and the axes intersect at the center point 166 of the inner cavity of the bone.

The size and shape of the cortical bone 140b in cross-section 160 is significantly different from the cortical bone 140a shown in cross-section 150. The ridge 168 on the anterior surface of the bone is shifted in a lateral direction relative to the center 166 of the cavity, shown by arrow 151, relative to the location of the tibial tuberosity 158 on the anterior portion of the cross-section 150 relative to the center 156. The lateral shift of the ridge 168 can be measured in terms of an angle of rotation about the center of the cavity at that level of the bone. This rotation may be up to 70.degree. from epiphysis to diaphysis, depending on an individual patient's tibial anatomy. While FIG. 4B shows a ridge 168 that is shifted in a lateral direction 151, the ridge 168 may shift in a medial direction, particularly in more distal parts of the tibia. An anatomic implant stem can be designed to conform to the shape and rotation of the anterior ridge to improve fixation and rotation resistance. For example, the implant stem may include an anterior ridge that also rotates from a proximal portion of the stem to the distal portion to account for the rotation of the ridge 168. Additionally, the posterior portion 169 of the bone is now rounded compared to the posterior side 159 of the cross-section 150, with no indent in the posterior portion 169. Furthermore, the medial side 165 and lateral side 167 are more rounded compared to the medial side 155 and lateral side 157 of cross-section 150. The changes in the shape of the bone create new landmarks for an anatomic stem to accommodate, and changes in the size of the cancellous bone portion provides a smaller cavity into which the stem is implanted.

Figure 4C:
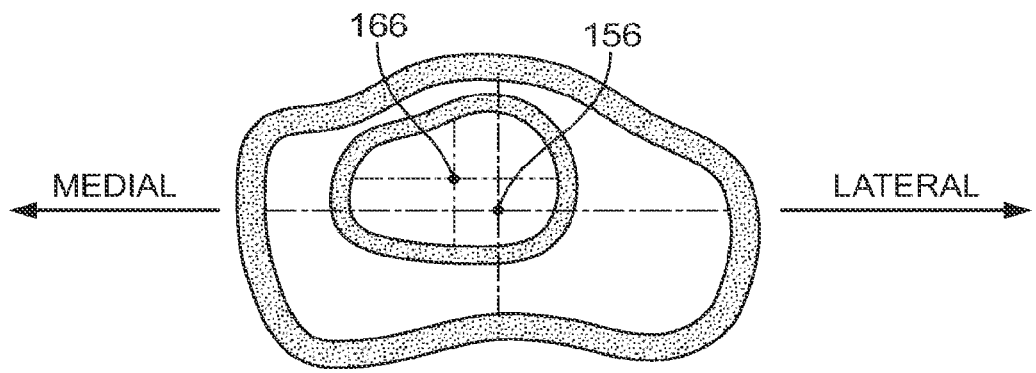
FIG. 4C shows an overlay of the cross-sections shown in FIGS. 4A and 4B.

In addition to the changes in the size and shape of the inner bone cavity between the cross-sections 150 and 160, the center point 166 of the cross-section 160 is shifted relative to the center point 156 of the cross-section 150. The movement of the center point of the inner bone cavity is highlighted in FIG. 4C, which shows an overlay of the cross-sections 150 and 160. The center point 166 in the distal cross-section is shifted in an anteromedial direction relative to the center point 156 in the proximal cross-section. The shift may be caused by the sharper tapering angle of the lateral side of the bone compared to the medial side of the bone discussed above with respect to FIG. 2. In other tibia bones, the center point 166 may shift in other directions due to variations in patient tibial anatomy. For example, the center point may shift in an anterior direction, a medial direction, a lateral direction, or an anteromedial direction. Alternatively, the center point may shift in a posterior direction, although generally tibial anatomies will likely shift in an anterior direction, if any shift in the anterior-posterior direction is present. In other bones, for example in patients having a different tibial anatomy, the center points 156 and 166 may be co-located and not shifted relative to each other.

The combination of changes in the size, position, and shape of the inner cavity of the bone from proximal to distal cross-sections create a need for changes in the design of a tibial stem to maintain an adequate interface with the bone anatomy at different levels of the tibia. In order to maintain the alignment of the stem with the center of the intramedullary cavity, the stem is designed so that the center point of the stem shifts from the proximal to the distal end of the stem in order to accommodate the shift from the center point 156 to the center point 166. In addition, the overall size of the stem can be varied, as the cavity in the proximal cross-section 150 is much larger than the inner cavity of the distal cross-section 160. In order to maintain a close interface with the cortical bone 140 and transmit forces to the bone, the stem shape preferably also changes to accommodate the changing contours and landmarks of the proximal and distal cross-sectional shapes. Although the size, shape, and center of an anatomic stem may change between a proximal cross-section and a distal cross-section of the stem to accommodate corresponding changes in bone anatomy, the aspect ratio may remain generally constant. The generally constant aspect ratio, or any other characteristic of the bone that remains generally constant, can provide an improved approximation of bone anatomy and allow the implant to fit a larger population of patient bone sizes.

Figure 5:
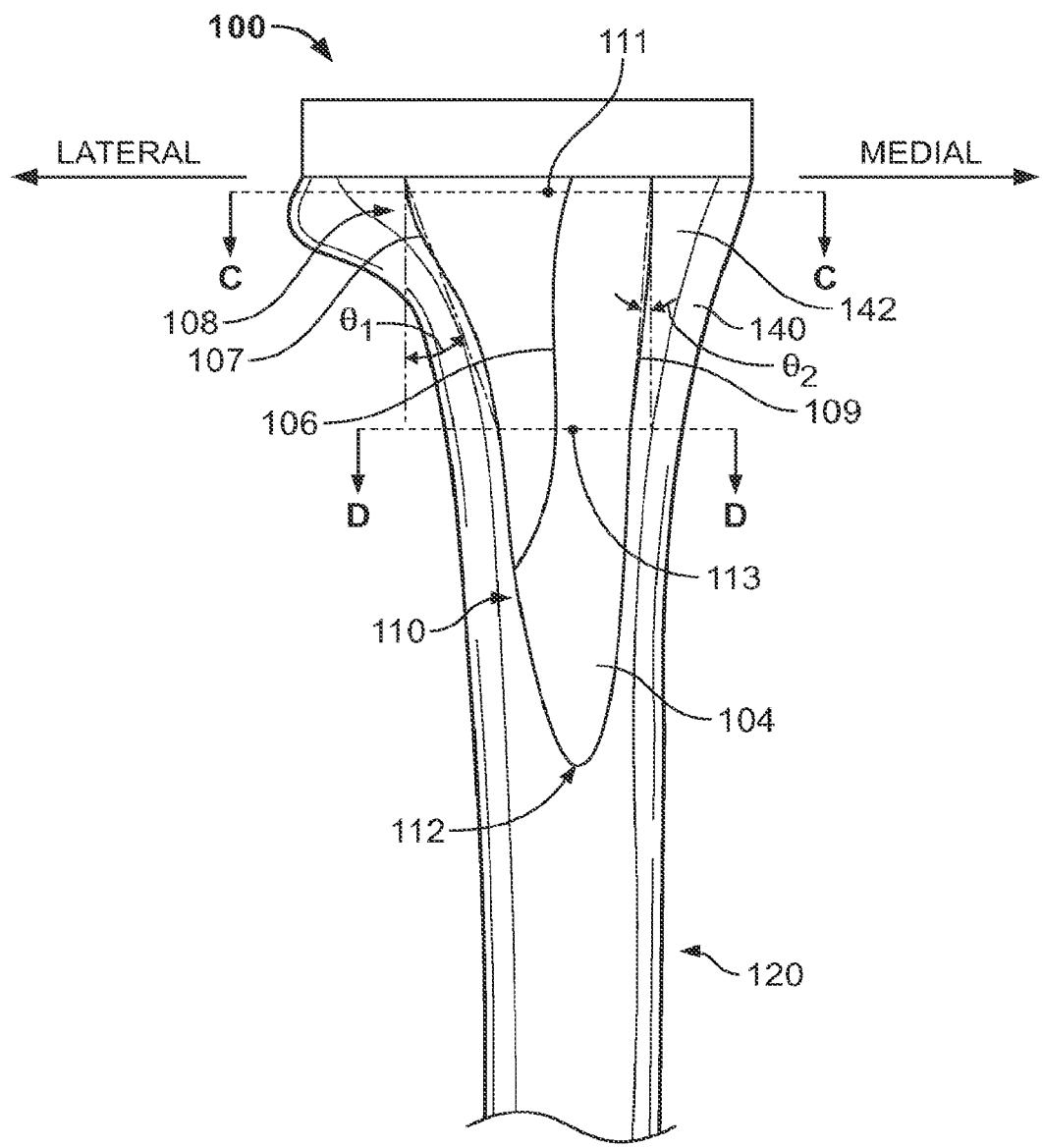
FIG. 5 shows the tibial implant of FIG. 1 implanted into the tibial bone of FIG. 2.

The close interface with the varying anatomy of the tibial bone provided by an anatomic stem is shown in FIG. 5, which depicts the tibial implant 100 of FIG. 1 implanted into the tibial bone 120 of FIG. 2. The varying size and shape of the stem 104 from the proximal end to the distal end of the stem accommodates variations in the cross-sectional anatomy of the bone 120 at the different levels along the longitudinal axis of the bone. For example, the upper portion 108 of the stem 104 is wider than the lower portion 110 of the stem to accommodate the larger size of the inner cavity of the cancellous bone 142 in the proximal region of the bone 120. As the upper portion 108 tapers from line CC to line DD, the lateral side 107 of the upper portion 108 tapers at a sharper angle $\theta_1$ than the tapering angle $\theta_2$ of the medial side 109, thus shifting the center point 111 of the stem 104 at proximal line CC medially to center point 113 at distal line DD to accommodate the corresponding shifting center of the bone 120.

The close interface between the stem 104 and the bone 120 is shown by cross-sectional views at different levels of the bone 120, for example at the levels indicated by lines CC and DD in FIG. 5. The lines CC and DD correspond to the lines AA and BB discussed above with respect to FIG. 2, with the line CC above the critical point of inflection of bone 120 and the line DD below the point of inflection.

Figure 6A:
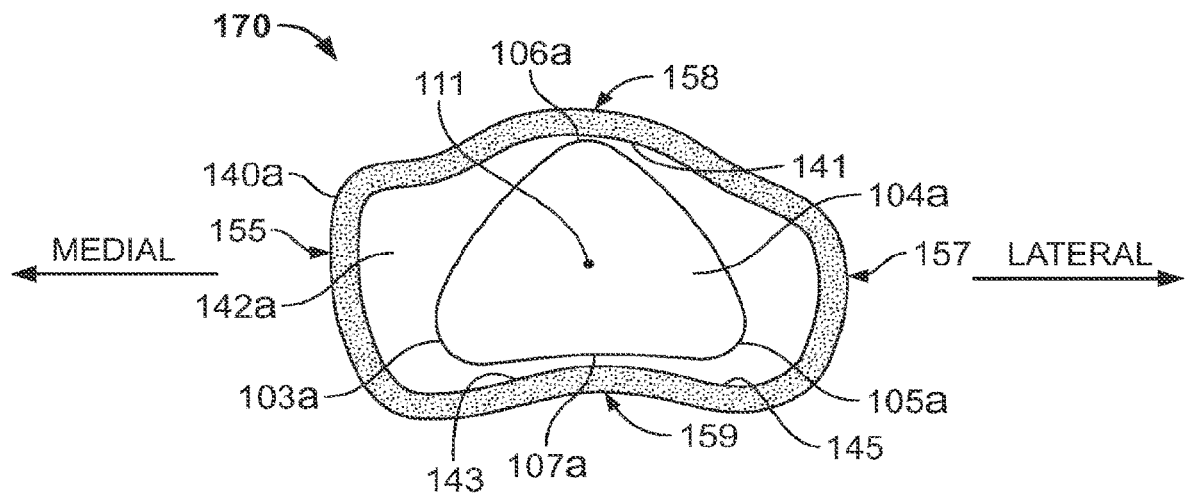
FIGS. 6A and 6B show illustrative transverse cross-sections of the implant and bone shown in FIG. 5.

FIG. 6A shows a cross-section 170 of the implant 100 in bone 120 taken at the line CC in FIG. 5. In cross-section 170, the stem 104a fills a significant portion of the inner cavity formed by the cancellous bone 142a. The stem 104a also includes rounded corners 103a, 105a, and 106a that provide stabilization and an interface between the stem 104a and the cortical bone 140a. For example, the rounded corner 106a is positioned near the cortical bone 140a of the tibial tuberosity 158 adjacent inner surface 141 of the cortical bone 140a. In addition, the corners 105a and 103a extend toward the lateral and medial sides of the bone while the posterior side 107a between the two corners accommodates the notch on the posterior side 159 of the bone. The shape of the stem 104a defines an aspect ratio between the width of the implant from corner 103a to corner 105a and the height of the implant from corner 106a to posterior side 107a. In certain embodiments, the aspect ratio may be between about 0.5 and about 4.0, between about 1.0 and about 2.0, or may be any other suitable value to accommodate varying patient anatomies. Modeling bone anatomy across a patient population may establish an aspect ratio range used in the design of anatomic implants. For example, data shown in FIG. 9 and discussed below shows aspect ratios of various intramedullary cavities that have aspect ratios generally falling in the range 1.5+/−0.4.

The position and shape of the side 107a allows a surgeon to place the stem 104a into the bone without hitting the posterior side 159 of the bone. The position of the three corners also provides anti-rotation contact between the stem 104a and cortical bone 140a. While a torsional force applied to the stem 104a may move the stem a small amount, interfering contact is created at least between one of the corners 103a and 105a and the inner surfaces 143 and 145 of the posterior side 159 of the cortical bone, and also between the rounded corner 106a and the inner surface 141 of the tibial tuberosity 158.

Figure 6B:
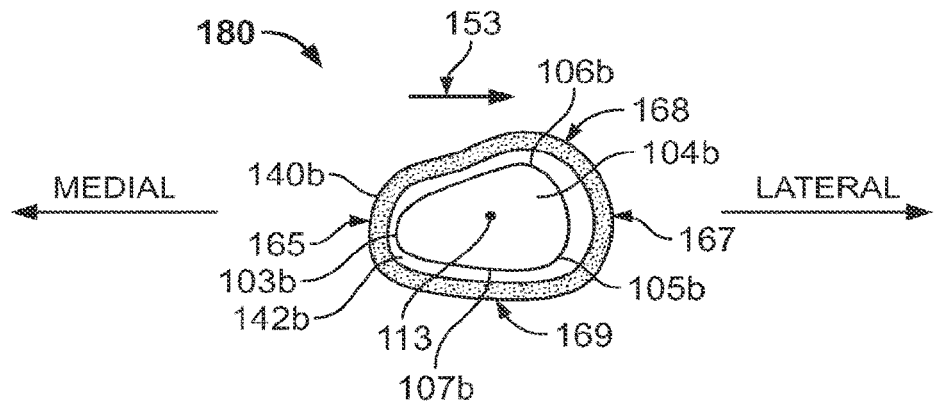
Figure 6C:
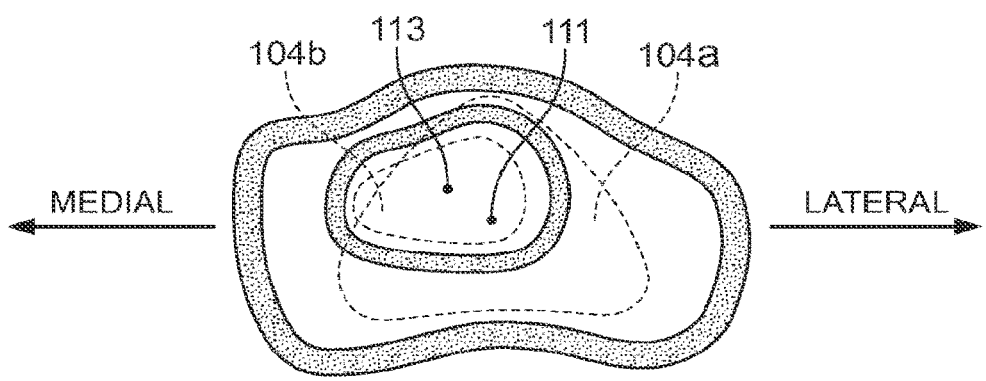
FIG. 6C shows an overlay of the cross-sections shown in FIGS. 6A and 6B.

Changes in the stem 104 that accommodate corresponding changes in the bone anatomy are shown in a second transverse cross-section viewed at a distal region of the bone. FIG. 6B shows a cross-section 180 taken at the level of line DD shown in FIG. 5. In the cross-section 180, the size and shape of the stem 104b is changed to accommodate the varied anatomy. The rounded corner 106b on the stem 104b is shifted in a lateral direction, shown by arrow 153, as the anterior ridge 168 of the bone has moved laterally in the direction of arrow 153 relative to the tibial tuberosity 158 on the anterior side of the bone in the proximal region. The tibial implant stem is designed such that it generally mimics the shape of the tibial intramedullary cavity and takes into account the rotation of this ridge. The lateral shift of the ridge 168 can be measured in terms of an angle of rotation about the center of the bone, and the rotation may be up to 70.degree. from a proximal portion of the stem to the distal portion of the stem. FIG. 6C illustrates the relative change in the stem from proximal to distal portions to accommodate the tibial intramedullary cavity and the rotation of the ridge 168. The rounded corner 106a of the implant stem 104a in cross-section 170 is shifted laterally in the distal cross section 180 of the implant stem 104b to enhance fixation against cortical bone throughout the bone cavity. The rounded corners 103b and 105b are closer together, and the side 107b is shorter, to accommodate the decreased width of the inner cancellous bone 142b.

The cross-section 180 shows the interaction between the stem 104b and the cortical bone 140b that provides resistance to movement cause by torsional forces applied to the stem 104b. As in the cross-section 170, rotation of the stem 104b in the cross-section 180 causes interfering contact between rounded corner 106b and the anterior ridge 168 of the cortical bone 140b as well as between one of rounded corners 103b and 105b and the posterior side 169 of the bone. Because the interfering contact is maintained from the proximal portion to the distal region of the stem, the rotation of the stem is resisted and the torsional forces applied to the stem are distributed along the longitudinal access of the stem into the surrounding cortical bone in both the proximal and distal regions.

In addition to the differential size and shape of the stem between the cross-section 170 and the cross-section 180, the distal center point 113 of the stem is shifted relative to the proximal center point 111 to maintain alignment with the changing center point of the bone. The shift from center point 111 to center point 113 is shown in FIG. 6C, which shows an overlay of cross-sections 170 and 180. The overlay shows the distal stem 104b shifted anteromedially relative to the distal stem 104a. The shift, caused by the uneven tapering of the stem, mimics the uneven tapering of the tibia and accommodates the shifting center point of the intramedullary cavity. In other implementations, for example for implants designed based on different tibial anatomies, the center points 111 and 113 may be co-located, and the distal stem 104b may not be shifted relative to the distal stem 104a, or the center point 113 may shift laterally relative to the center point 111.

In certain implementations, an anatomic stem of a tibial implant may match the shape of a specific distal cross-section of the intramedullary canal and leverage this shape to provide improved fixation over traditional cylindrical shapes. This anatomic stem may use a single shape, but change in size from the proximal to distal end. Additionally, the stem may have a center aligned with the distal cross-section to guide insertion. For example, a distal cross-sectional shape, such as the tear-drop shape shown in the cross-section 180, or an oval shape, may be used for the implant stem shape. In this case, the tear-drop shape of the stem 104b is used over the length of the stem. The stem may also be offset or angled from the center of the tray to accommodate for the changing center of the tibial intramedullary cavity. In other implementations, the shape of the anterior wall or ridge may be leveraged to provide improved fixation. A stem may be designed to conform primarily to the anterior portion of the tibial intramedullary canal to provide improved rotation resistance and fixation against the anterior ridge.

Additional methods for taking advantage of the tibial anatomy may include using fixation elements, such as bone screws, to change an implant's effective shape. A tibial implant may be cannulated so that a bone screw passes through the stem and provides additional fixation with the bone. For example, an implant may have an opening that runs longitudinally down the stem so that a bone screw may engage the intramedullary canal near or through the anterior ridge to provide additional fixation. Furthermore, a screw opening may be provided in other areas of the stem or tray to provide additional support. For example, a screw hole may be provided as a cutout on a side of the tray to wedge the implant against bone. At the level of the stem at which the screw exits the stem and enters surrounding bone, the effective shape of the stem is changed in the direction the screw exits, as the cross-section taken at that level includes both the stem and the additional screw material.

Figure 7:
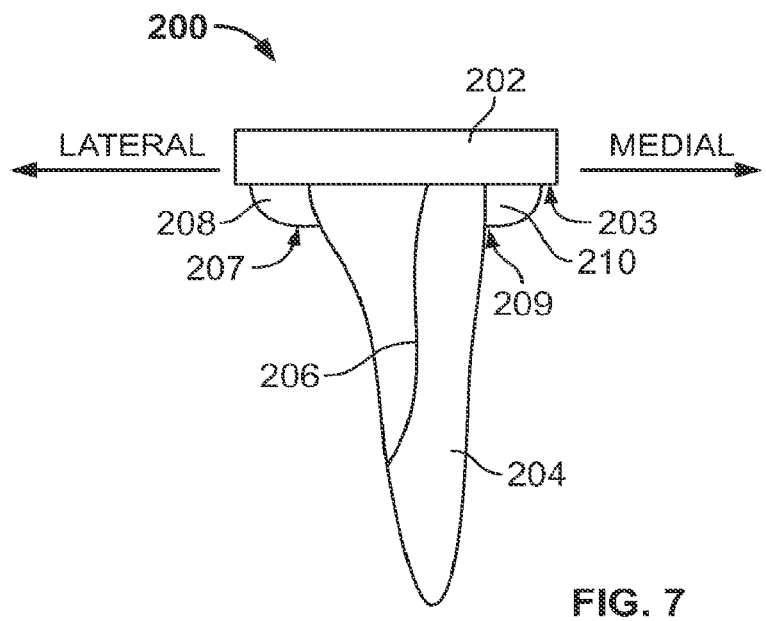
FIG. 7 shows an illustrative tibial implant having an anatomic stem and fin extensions.

The close interface between an implant and bone provided by an anatomic stem can be supplemented with one or more additional fixation features. In areas where there is more cancellous bone between the implant and cortical bone than other areas, for example in the proximal region of the tibia that exhibits a wider intramedullary cavity, such fixation features can be disposed to supplement the fixation of the stem and reduce the negative effects of stress shielding and rotation. A proximal portion of the stem that is placed into the wider region of the intramedullary cavity can incorporate fixation extensions to maintain a close bone interface. FIG. 7 shows an example of a tibial implant 200 that includes fixation extensions, with fin extensions 208 and 210 extending outward from the stem 204 and the bottom surface 203 of the tray 202. When the implant 200 is placed into a tibia, the fin extensions 208 and 210 extend into the spongy cancellous bone of the intramedullary cavity and supplement the stress transmission and rotation resistance of the anatomic features of the stem 204, such as the rounded corner 206. Though the cancellous bone is not as strong as cortical bone, the contact between the fins 208 and 210 and the cancellous bone provides added stability to the implant 200, as rotation of the implant would require additional force to both overcome the contact between the stem 204 and the cortical bone and crush the cancellous bone contacting the fins 208 and 210. In order to facilitate insertion of the implant 200 into the bone without crushing the cancellous bone, the inferior perimeters 207 and 209 of the fins 208 and 210 can include a tapping mechanism, such as a knife edge, that creates a seam in the cancellous bone rather than crushing it down.

The fin extensions may also facilitate insertion of an anatomic implant into an intramedullary cavity at an offset angle so that the stem is inserted without impinging on cortical bone. The non-symmetrical shape of the anatomic stem and the changing bone anatomy may cause interference if the implant is inserted straight into the bone. The straight insertion into the bone, however, is easiest for a surgeon to perform and requires force to be applied to the implant in only one direction down into the bone. This straight insertion is difficult to accommodate if an anatomic stem has a corner or other feature that rotates to match distal anatomy but interferes with proximal cortical bone if the stem is inserted straight into the intramedullary cavity. In order to accommodate the anatomy and the shape of the stem, the anatomic implant is rotated as it is inserted into the bone to avoid interference from the cortical bone. Fin extensions, such as the fins 208 and 210 in implant 200, can be designed to guide the twisting rotation of the implant during insertion such that the surgeon can insert the implant with a single force down into the bone, with the fins guiding the twisting rotation of the implant during insertion. Such fins are designed with a curved or corkscrew-shaped profile extending distally down the stem from the implant tray. The fins engage the cancellous bone, and the twisting shape of the fins translates the axial insertion force into a rotational force that rotates the implant through a desired angle as it is inserted. The fin shape and resulting insertion rotation provide for insertion of the stem with only an axial force, simplifying the implantation for the surgeon, while still rotating the implant to reduce potentially harmful contact between the implant and cortical bone.

As the anatomic implant is inserted further into the intramedullary cavity, a rounded corner of the stem may begin to engage the anterior ridge of the intramedullary cavity. The anatomic stem may follow the rotation of the anterior ridge while moving distally until the tibial tray is seated against the proximal bone cut. To guide twisting during placement, curved or corkscrew-shaped fins may extend from the implant. These curved fins may engage cortical or cancellous bone to act as a guide for twisting the implant in addition to providing additional fixation to bone. The end of the curved fin may act as a reference point for twisting. For example, the end of a curved fin may be lined up with a major or minor axis of the proximal tibial cut prior to entering the bone. As the curved fins are twisted into the bone, the distal movement of the stem may be synchronized with the twisting to accurately guide placement of the implant.

Figure 8A:
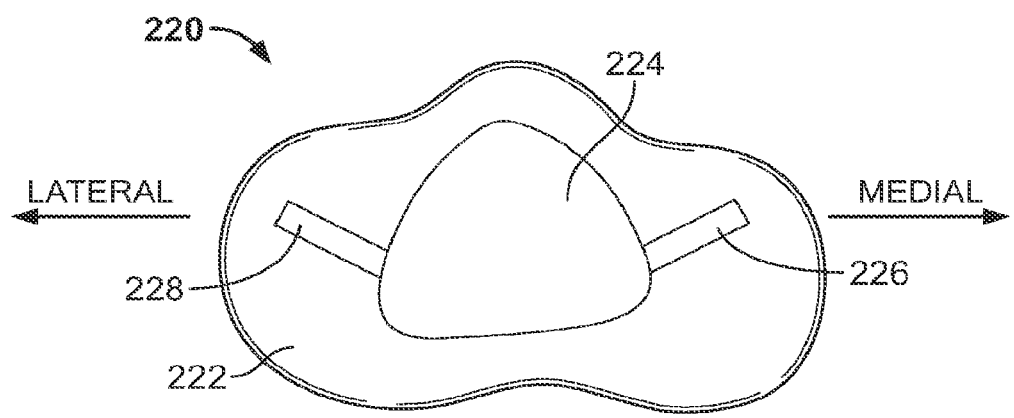
FIGS. 8A and 8B show bottom views of illustrative tibial implants having an anatomic stem and fin extensions.

The outward extension of fins on the tibial implant extends the interface between the bone and implant into areas of the bone where the stem does not extend in close proximity to the cortical bone. FIG. 8A shows an implant 220 having fin extensions 226 and 228 extending outward from stem 224 and bottom surface 222. The fins 226 and 228 extend into areas of the bottom surface 222 in which there is a larger area of the surface between the stem 224 and the perimeter of the surface. By extending into these areas, the fins 226 and 228 provide a closer interface with surrounding bone when the component 220 is implanted, and the bottom surface 222 abuts a patient's tibia.

Figure 8B:
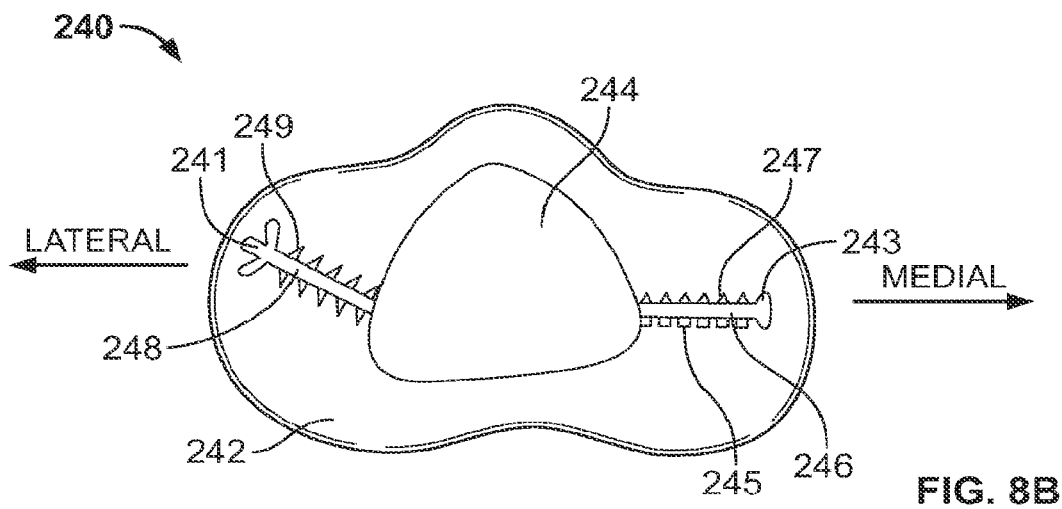

In order to further supplement the fixation of an anatomic stem, fin extensions can include fixation elements that increase the surface area on which the fins contact surrounding bone. The fixation elements may include the shape of the fins or further extensions off of the fins, as shown in FIG. 8B. An implant 240 includes two fin extensions 246 and 248 that extend outward from stem 244 and bottom surface 242 of the implant. In contrast to the fin extensions 226 and 228, each of fin extensions 246 and 248 include an outer portion that is shaped to supplement bone engagement and individual engagement portions extending outward perpendicular to the angle at which the fin extends from the stem 244.

The outer portions of the fin extensions 246 and 248 are shaped as a rounded tip 243 and a cloverleaf 241, respectively, but any suitable shape may be used. The shaped outer portion increases the surface area over which the fins 246 and 248 contact cancellous bone when the component 240 is implanted, and may also supplement contact between the stem 244 and outer cortical bone. When the component 240 is implanted and the bottom surface 242 abuts a tibial bone, the engaging outer portions 243 and 241 of the fins can further limit the angle over which the implant 240 can be rotated before interfering contact is made with cortical bone. While an implant having an anatomic stem without fins can rotate until a corner of the stem contacts cortical bone, the outer portions 241 and 243 may contact cortical bone before a corner of the stem 244 contacts the bone, and thus may limit the possible rotation angle more than if the implant 240 included only the stem 244.

The engagement portions 245, 247, and 249 that extend outward from fins 246 and 248 supplement the fixation provided by the fins. While the engaging extensions are shown as square projections 245, triangular projections 247, and sawtooth projections 249, the extensions may have any other suitable shape. The engagement portions further increase the surface area of contact between the fins and the cancellous bone and also provide resistance to movement in directions other than rotation of the implant. For example, the square projections 245 and triangular projections resist movement in a direction parallel to the direction in which the fin 246 extends from the stem 244, and the sawtooth projections 249 resist movement in a direction parallel to the direction in which the fin 248 extends from the stem 244.

Other suitable shapes for the fin extensions, outer portions, and engagement portions may provide various advantages in improving fixation, resistance to rotation, and guidance during insertion. Shapes that may be too costly or otherwise difficult to form using standard machining or casting techniques may be formed using rapid manufacturing techniques. For example, standard machining techniques may not be able to form corkscrew shapes or clover-shaped edges due to limitations of the machining tools, but rapid manufacturing machinery can create these shapes with precision. Fin extensions, including the outer portions and engagement portions, can also be formed integrally with the implant with rapid manufacturing techniques. Additionally, rapid manufacturing facilitates the creation of fin extensions, and nuanced stem designs, for a specific patient. Patient-specific implants designed with fin extensions, including engagement portions, may provide a better fit with the surrounding bone or may take into account a patient-specific deformity or medical condition. For example, it may be advantageous to design a specific fin shape, outer portion shape, engagement portion shape, or arrangement of the three to accommodate for diseased or missing bone for a specific patient to provide fixation not offered by a standard implant designed for a larger population of patients.

The features and variations of the tibial anatomy used to design an anatomic tibial implant are obtained by imaging and modeling the intramedullary cavities of a population of patients. To model the tibia, imaging data is acquired using medical imaging techniques. The model is then viewed at various cross-sectional views at different depths of the bone to study the size, shape, and changes of the intramedullary anatomy. Non-limiting examples of medical imaging techniques used to obtain the bone models include x-ray, computed axial tomography, magnetic resonance imaging (MM), and ultrasound. The features extracted from the model at various levels of the bone are then used to design the tapering and changes in shape and size of the implant stem so that the anatomical implant provides a better fit against cortical bone in the tibial intramedullary cavity.

In some implementations, the imaged tibial anatomy of multiple patients is combined into a composite model to be used in designing a robust anatomic implant that provides an improved fit, and improved fixation, over a varied patient population compared to a standard implant. The composite model provides a comparison of the different anatomies across the studied population, including the variations in shapes and sizes that are accommodated by the anatomic implant. The range of variations in the modeled bones are summarized by defining two conditions indicating the largest and smallest cavity anatomies across the population at each level of the bone. The maximum and minimum limits are defined by a "maximum-material condition" (MMC) and a least-material condition (LMC). The MMC is defined by superimposing the models of all of the bones studied and creating an envelope along the outer-most boundary of the superimposed model throughout the intramedullary cavity. The LMC is then defined by creating an envelope along the inner-most boundary of the superimposed model throughout the cavity. The MMC and LMC act as limits, and the anatomy of the intramedullary cavities of each bone studied falls either on or between these two limits at each level of the bone. Thus, the MMC and LMC define the full range of anatomies that the anatomic implant accommodates, and these two conditions are used to design the anatomic stem. Because the MMC represents the largest cavities, an implant designed to match the MMC may break into cortical bone at some locations of the intramedullary cavity when implanted into bones that are smaller than the MMC in some areas. Thus, it is preferable to design the anatomic stem to match the LMC model, as that model is at least as small as the intramedullary cavity of each bone in the population at all levels of the bone. For a bone having the intramedullary cavity of the MMC condition, the LMC-designed stem may not contact the cortical bone at all levels of the bone, but may still provide an improved fit over a standard implant by accommodating anatomical changes and variations that are extracted from the LMC model. In other embodiments, an anatomic implant can be designed to match the MMC model, or a combination of the MMC and LMC.

In some implementations, a tibial anatomy model of a single patient's bone is used to design a "patient-matched" implant for the specific patient's anatomy. The patient-specific implant accommodates the variations and features of the patient's tibial anatomy and provides close fit with the patient's cortical bone. The precision in the design provides improved fixation and fit compared to a standard implant designed for implantation into a wide variety of tibial bone anatomies.

Figure 9:
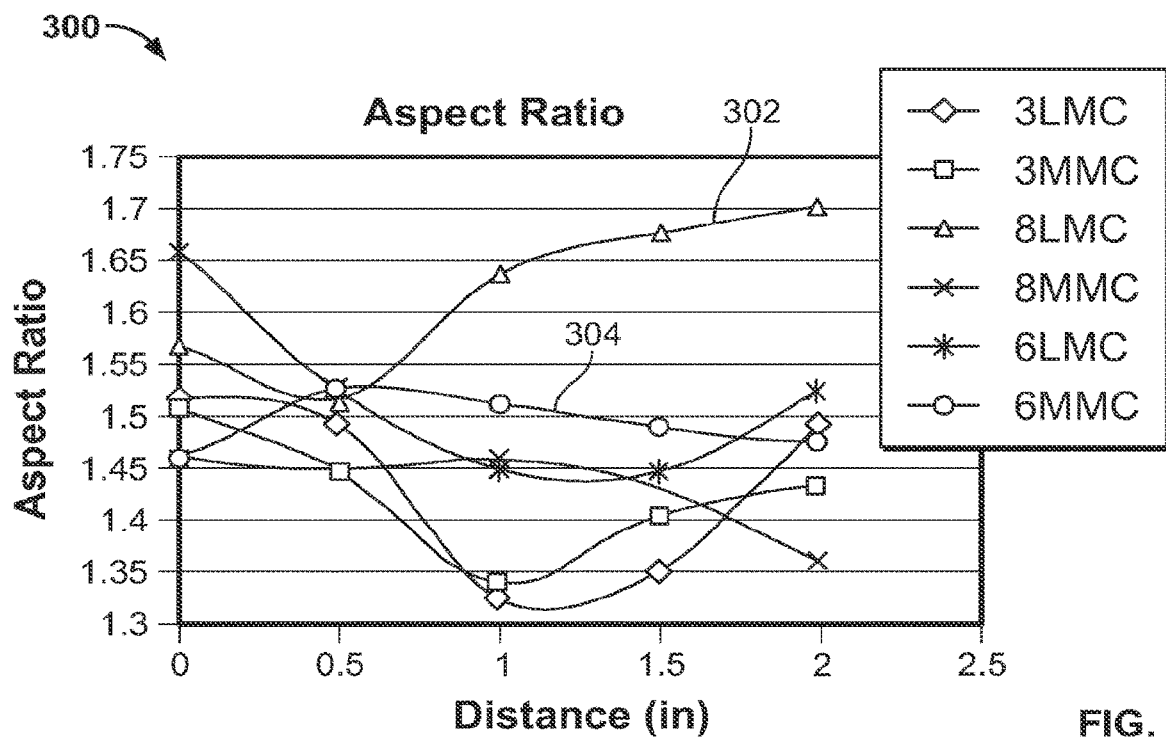
FIG. 9 shows aspect ratio data for tibial intramedullary cavities.

Modeling tibial bones for a single patient or across a population of patients provides useful data on the changes and trends in the different areas of the bone that dictate implant design. In some instances, rather than exhibiting large changes from one area of the bone to another, features extracted from the model may exhibit a generally consistent trend that can be leveraged in designing an implant. For example, although the size and shape of the intramedullary cavity changes throughout the tibial bone, the aspect ratio of the cavity measured at different levels of patient bones exhibits a consistent trend. FIG. 9 shows a graph 300 that plots the aspect ratio measured from cross-sections taken along tibial intramedullary cavities from a reference location to a distal location across a patient population of tibia bones. The reference location may be at the knee joint, at a proximal bone cut such as the lines CC or DD in FIG. 5, or another suitable reference point. The location of each cross-section plotted is measured as a location, in inches in FIG. 9, in inches from the reference point. The groups of tibia bones plotted in graph 300 include smaller bones ("size 3"), average bones ("size 6"), and larger bones ("size 8"). For each bone size, a sample of bones was imaged to model the population of bones of that particular size, and a computer model was generated using the techniques discussed above. A composite model of each size of bones was then used to define a LMC and a MMC for each group. Aspect ratios were calculated for the LMC and MMC models for each bone size at cross-sections taken at multiple levels of the bone.

The bones modeled in FIG. 9 exhibit aspect ratios generally falling in the range 1.5+/−0.2. For example, line 302 shows the aspect ratio trend of the LMC of the "size 8" bones. The aspect ratio of the LMC for those bones is about 1.55 at a proximal bone cut of the tibial intramedullary cavity and varies by about 0.15, to a value of about 1.70 at a distal cross-section taken two inches from the bone cut. As a comparison, line 304 shows the aspect ratio of the MMC "size 6" bones, a different bone size and material condition than line 302. At a proximal bone cut, the aspect ratio of this model is about 1.45 and varies by about 0.4 through the cross-sections, to a distal cross section where the aspect ratio is about 1.47. The other models plotted in FIG. 9 also show different trends, but all data points fall within the fairly narrow range of 1.5+/−0.2 for all sizes, conditions, and levels of the models. This narrow range is leveraged in design of an anatomic stem by maintaining the aspect ratio of the stem within this range at various levels of the stem while size and shape are varied to match corresponding changes in the modeled anatomy.

Figure 10:
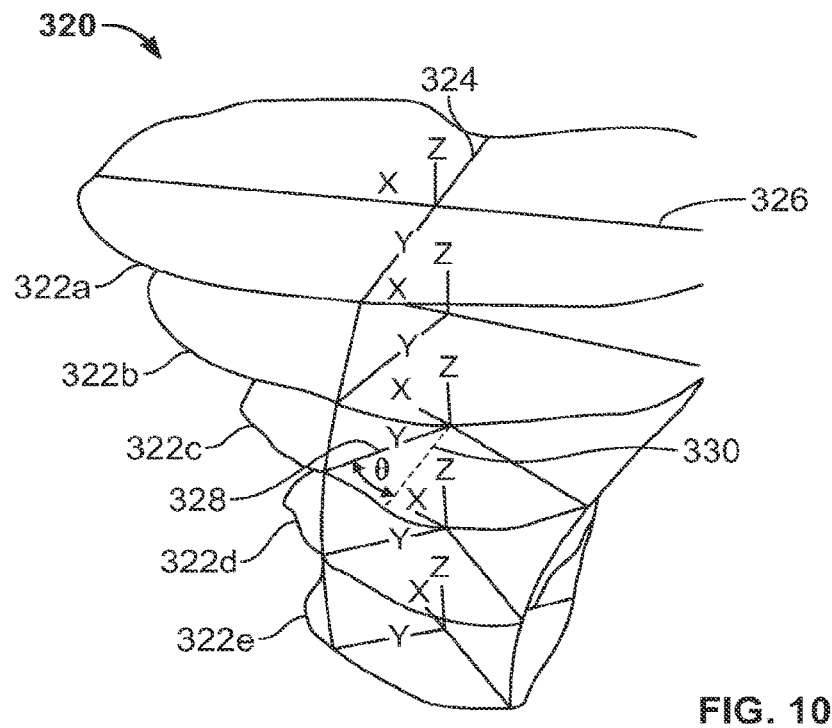
FIG. 10 shows a wireframe model of cross-sections of a tibial intramedullary cavity.

In addition to extracting trends in aspect ratio of the modeled bones to design an anatomical implant, the shift and rotation of the tibial anterior ridge can be measured in the models and used to design a corresponding change in an anatomic stem. FIG. 10 shows a wireframe model 320 of cross-sections 322*a*-*e* of a tibial intramedullary cavity where the anterior ridge or prominence of the bone shifts by an angle about the center of the bone. The wireframe model 320 may be created using data from a single patient, or may be a model of the LMC or MMC of bones imaged across a patient population. The shift in the ridge and the anterior portion of the intramedullary cavity is the result of the changing cross-sectional shape of the tibia. The shift in the anterior portion of the intramedullary cavity caused by this shape change is shown in wireframe model 320 by the major and minor axes of each of the cross-sections 322a-e, for example minor axis 324 and major axis 326 shown for cross-section 322a. The major and minor axes of the cross-sections rotate about the longitudinal axis of the tibia as cross sections are taken moving distally down the tibia from cross-section 322a. For example, the short axis 328 of cross-section 322c is rotated by an angle θ in the plane of the cross-sections from the short axis 324 of cross-section 322a, represented by a dotted line 330 in the cross-section 322c. This angle θ shows the angle of rotation of the anterior ridge at the level of cross-section 322c and generally increases moving distally down the tibia.

The rotation of the anterior ridge is accounted for in the design of the anatomic implant stem by including a corresponding ridge feature on the stem. For example, the angle of rotation of the modeled ridge is used to enhance the fit of the anatomic stem by defining the extent to which a rounded corner, such as rounded corners 106a and 106b of implant 100, shift or rotate along the implant stem to conform to the tibial intramedullary cavity. The enhanced fit provides rotation resistance and resists loosening of the implant postoperatively by seating the implant against structural cortical bone, as opposed to spongy cancellous bone, over the length of the stem. Depending on the anatomy of the bone or bones modeled to create a model, the rotation of the short axis of the modeled cross-sections may be between 0.degree. and 70.degree. over the length of the stem from a proximal end to a distal end.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A tibial implant, comprising:
a tray configured to abut a patient's bone; and
a stem extending from a surface of the tray, said stem having:
a proximal portion at which a first cross-section of the stem has a first shape and a first center positioned at a first location relative to the tray; and
a distal portion at which a second cross-section of the stem has a second shape and a second center positioned at a second location relative to the tray, the second shape is different than the first shape, the second center of the distal portion of the stem is positioned medially of the first center of the proximal portion of the stem;
a fin extending outward from the stem; and
a plurality of engagement portions extending from the fin;
wherein the fin extends from the stem at a first angle relative to a longitudinal axis of the stem, and each of the plurality of engagement portions extends from the fin at a second angle perpendicular to the first angle.

2. The tibial implant of claim 1, wherein the fin is a first fin, the implant further comprising a second fin extending outward from the stem, the second fin extending in a different direction than the first fin.

3. The tibial implant of claim 1, wherein the fin is arranged and configured to extend into cancellous bone of an intramedullary cavity of a patient's bone to resist relative rotation of the implant.

4. The tibial implant of claim 1, wherein the fin extends from an inferior surface of the tray.

5. The tibial implant of claim 1, wherein an inferior perimeter of the fin is configured to cut into a patient's bone.

6. The tibial implant of claim 1, wherein the fin is arranged and configured to guide twisting rotation of the implant during insertion.

7. The tibial implant of claim 1, wherein the fin includes a length extending from the stem towards an outer tip, the length of the fin including a curved or corkscrew-shaped profile.

8. The tibial implant of claim 1, wherein the fin includes an outer portion arranged and configured to engage a patient's bone, the outer portion including one of a rounded tip, a hook shaped end portion, and a cloverleaf shape.

9. The tibial implant of claim 1, wherein the plurality of engagement portions include a shape selected from one of a square projection, a triangular projection, a sawtooth projection, a circular projection, or combinations thereof.

10. The tibial implant of claim 1, wherein the proximal portion of the stem includes a lateral side and a medial side, the lateral side of the proximal portion of the stem tapering at a first angle, the medial side of the proximal portion of the stem tapering at a second angle, the taper of the first angle being greater than the taper of the second angle.

11. The tibial implant of claim 1, wherein the second shape has a cross-section area that is less than the cross-sectional area of the first shape.

12. The tibial implant of claim 1, wherein the tibial implant is monolithic.

13. A tibial implant, comprising:
a tray configured to abut a patient's bone; and
a stem extending distally from an inferior surface of the tray, the stem including:
a proximal portion at which a first cross-section of the stem has a first shape and a first center positioned at a first location relative to the tray;
a distal portion at which a second cross-section of the stem has a second shape and a second center positioned at a second location relative to the tray, the second shape is different than the first shape, the second center of the distal portion of the stem is positioned medially of the first center of the proximal portion of the stem;
a first fin extending from the stem in a first direction;
a second fin extending from the stem in a second direction, the second direction being different than the first direction; and
a plurality of engagement portions extending from the first and second fins.

14. The tibial implant of claim 13, wherein:
the first fin extends from the stem at a first angle relative to a longitudinal axis of the stem;
the second fin extends from the stem at a second angle relative to the longitudinal axis of the stem;
each of the plurality of engagement portions extending from the first fin extend from the first fin at a third angle; and
each of the plurality of engagement portions extending from the second fin extend from the second fin at a fourth angle.

15. The tibial implant of claim 14, wherein the third angle is perpendicular to the first angle and the fourth angle is perpendicular to the second angle.

16. The tibial implant of claim 13, wherein the first and second fins each extend from the inferior surface of the tray.

17. The tibial implant of claim 13, wherein each of the first and second fins include a length extending from the stem towards an outer tip thereof, the length of the fins including a curved profile.

18. The tibial implant of claim 13, wherein the plurality of engagement portions include a shape selected from one of a square projection, a triangular projection, a sawtooth projection, a circular projection, or combinations thereof.

19. A tibial implant, comprising:
a tray configured to abut a patient's bone; and
a stem extending distally from an inferior surface of the tray, the stem including a proximal portion and a distal portion, the proximal portion of the stem includes a lateral side and a medial side, the lateral side of the proximal portion of the stem tapering at a first angle, the medial side of the proximal portion of the stem tapering at a second angle, the taper of the first angle being greater than the taper of the second angle;
a first fin extending from the stem in a first direction;
a second fin extending from the stem in a second direction, the second direction being different than the first direction; and
a plurality of engagement portions extending from the first and second fins.

* * * * *